US010732187B2

(12) United States Patent
Parham

(10) Patent No.: US 10,732,187 B2
(45) Date of Patent: Aug. 4, 2020

(54) DIAGNOSTIC REAGENTS AND METHODS SPECIFIC TO INNER EAR DISORDERS

(71) Applicant: THE UNIVERSITY OF CONNECTICUT, Farmington, CT (US)

(72) Inventor: Kourosh Parham, West Hartford, CT (US)

(73) Assignee: The University of Connecticut, Farmington, CT (US)

(*) Notice: Subject to any disclaimer, the term of this patent is extended or adjusted under 35 U.S.C. 154(b) by 414 days.

(21) Appl. No.: 15/041,156

(22) Filed: Feb. 11, 2016

(65) Prior Publication Data

US 2016/0238617 A1 Aug. 18, 2016

Related U.S. Application Data

(60) Provisional application No. 62/117,220, filed on Feb. 17, 2015.

(51) Int. Cl.
*G01N 31/00* (2006.01)
*G01N 33/53* (2006.01)
*G01N 33/68* (2006.01)

(52) U.S. Cl.
CPC ..... *G01N 33/6893* (2013.01); *G01N 2333/47* (2013.01); *G01N 2333/4727* (2013.01); *G01N 2800/14* (2013.01)

(58) Field of Classification Search
None
See application file for complete search history.

(56) References Cited

U.S. PATENT DOCUMENTS

| | | | |
|---|---|---|---|
| 5,776,179 | A | 7/1998 | Ren et al. |
| 5,885,225 | A | 3/1999 | Keefe et al. |
| 6,602,992 | B1 | 8/2003 | Dallos et al. |
| 2012/0122716 | A1 | 5/2012 | Lim et al. |
| 2014/0114209 | A1 | 4/2014 | Lodwig |
| 2016/0256083 | A1 | 9/2016 | Lodwig et al. |
| 2017/0150908 | A1 | 6/2017 | Nadon et al. |

FOREIGN PATENT DOCUMENTS

EP 1042726 B1 10/2000

OTHER PUBLICATIONS

Tascilar et al. (Annals of Oncology 10,Suppl. 4:S107-S110, 1999).*
Tockman et al. (Cancer Research 52:2711s-2718s, 1992).*
Sakaguchi et al. (Journal of Histochemistry & Cytochemistry, vol. 46, No. 1, 1998, pp. 29-39).*
Parham et al. Otolaryngology—Head and Neck Surgery 2014, vol. 15 (6), pp. 1038-1040.*
Chen (Hearing Research, 222, 2006, pp. 54-61).*
Chen, Guang-Di; "Prestin Gene Expression in the Rat Cochlea Following Intense Noise Exposure"; Hearing Research; 222; pp. 54-61; (2006).
International Search Report and Written Opinion; International Application No. PCT/US2016/017476; International Filing Date Feb. 11, 2016; dated May 13, 2016; 15 pages.
Parham et al.; "Inner Ear Protein as a Biomarker in Circulation?"; Otolaryngology—Head and Neck Surgery; Official Journal of American Academy of Otolaryngology—Head and Neck Surgery; 151(6) pp. 1038-1040; (2014).
Parham, Kourosh; "Prestin as a Biochemical Marker for Early Detection of Acquired Sensorineural Hearing Loss"; Medical Hypotheses; 85; pp. 130-133; (2015).
Rodoo, et al.; "Creatine Kinase MB (CK-MB) in Benign Paroxysmal Vertigo of Childhood: A New Diagnostic Marker"; Journal of Pediatrics; 146(4); pp. 548-551; (2005).
Parham et al.; "Inner Ear Protein as a Biomarker in Circulation?"; Otolaryngology—Head and Neck Surgery_Official Journal of American Academy of Otolaryngology; 151(6); pp. 1038-1040; (2014).
Andrade et al.; "Immunogold TEM of Otoconin 90 and Otolin—Relevance to Mineralization of Otoconia, and Pathogenesis of Benign Positional Vertigo"; Hear Res.; 292(1-2); pp. 14-25; (2012).
Deans et al.; "Mammalian Otolin: A Multimeric Glycoprotein Specific to the Inner Ear That Interacts with Otoconial Matrix Protein Otoconin-90 and Cerebellin-1"; PLoS One; 5(9); e12765; pp. 1-15, (2010).
He et al.; "Prestin at Year 14: Progress and Prospect"; Hear Res. 311; pp. 25-35; (2014).
Sacks & Parham et al.; "Preliminary Report on the Investigation of the Association Between BPPV and Osteoporosis Using Biomarkers"; Otology & Neurotology; 36; pp. 1532-1536; (2015).
Sakaguchi et al.; "Oncomodulin is Expressed Exclusively by Outer Hair Cells in the Organ of Corti"; The Journal of Histochemistry & Cytochemistry; 46(1); pp. 29-39; (1998).
Zheng et al.; "Prestin is the Motor Protein of Cochlear Outer Hair Cells"; Nature; 405; pp. 149-155; (2000).
Lee, Jehoon et al.; "Current Recommendations for Laboratory Testing and Use of Bone Turnover Markers in Management of Osteoporosis"; Clinical Chemistry; 32; pp. 105-112; (2012).
Avallone, Emilio et al.; "PS 1004-Otoli.-1i. Biological Fluids: A Possible Biomarker for Inner Ear Disease"; Poster; Paper presented at 41st Annual Association for Research in Otolaryngology Midwinter Meeting, Tuesday, Feb. 14, 2018, San Diego.
Dogan et al.; "Utilizing Prestin as a Predictive Marker for the Early Detection of Outer Hair Cell Damage"; Am J Otolaryngol., 39; pp. 594-598; (2018), https://doi.org/10.1016/j.amjoto.2018.07.007.
Hana, Randa Samir et al.; "Prestin Otolin-1 Regulation, and Human 8-oxoG DNA Glycosylase 1 Gene Polymorphisms in Noise-induced Hearing Loss"; 10, pp. 60-64; (2018).
Liba et al.; "Changes in Serum Prestin Concentration After Exposure to Cisplatin"; Otology & Neurotology; 38; pp. e501-e505; (2017).

(Continued)

*Primary Examiner* — Lisa V Cook
(74) *Attorney, Agent, or Firm* — Cantor Colburn LLP

(57) ABSTRACT

Described herein are compositions and methods for the detection of inner ear disorders such as balance disorders and hearing disorders resulting from acoustic injury, exposure to ototoxins, head trauma or viral illness. Specifically, otolin-1 and prestin have been verified as inner-ear specific biomarkers suitable for the detection of inner ear disorders.

15 Claims, 5 Drawing Sheets

Specification includes a Sequence Listing.

(56) References Cited

OTHER PUBLICATIONS

Micheel & Ball, Editors; "Evaluaion of Biomarkers and Surrogate Endpoints in Chronic Disease"; National Academies Press online; http://www.nap.edu/catalog/12869.html; 267 pages (2010).

Naples et al.; "Prestin as an Otologic Biomarker of Cisplatin Ototoxicity in a Guinea Pig Model"; Otolaryngology-Head and Neck Surgery Foundation; pp. 1-6; (2017); DOI: 10/1177/0194599817742093.

Parham et al.; "Inner Ear Protein as a Biomarker in Circulation?"; Otolaryngology-Head and Neck Surgery; 151(6); pp. 1038-1040; (2014).

Parham et al.; "Outer Hair Cell Molecular Protein, Prestin, as a Serum Biomarker for Hearing Loss: Proof of Concept"; Oncology & Neurotology; 37; pp. 1217-1222; (2016).

Parham et al.; Author Manuscript; "A Relationship Between Blood Levels of Otolin-1 and Vitamin D"; Otol Neurotol.39, pp. 2269-e273; (2018).

Tabtabai et al.; "Age-Related Increase in Blood Levels of Otolin-1 in Humans"; Otology & Neurotology; 38; pp. 365-869; (2017).

Evaluation of Biomarkers and Surrogate Endpoints in Chronic Disease; John R. Ball, Editor; The National Academies Press; Washington DC; ISBN 0-309-15130-9, 334 pages (2010).

Fettiplace, et al.; "Tonotopy in Calcium Homeostases and Vulberability of Cochlear Hair Cells"; Hearing Research; Retrieved from Internet; https://doi.org/10.1016/j.heares.2018.11.002;pp. 1-11.

Gillespie et al.; "Treating Hearing Disorders with Cell and Gene Therapy"; J. Neural Eng,; 11; 12 pages; (2014).

Hildebrand et al.; "Advances in Molecular and Cellular Therapies for Hearing Loss"; Molecular Therapy; 16(2); pp. 224-236; (2008).

Jain, et al.; "Cochlear Proteins Associated with Noise-Induced Hearing Loss: An Update"; Indian Journal of Occupational & Environmental Medicine: 2018; Vol. 22, No. 2, pp. 60-73.

Larsen, et al.; "Auto-Inflammatory Challenge of the Endolymphatic Sac—Cochlear Damage Measured by Distortion Product Oto-Acoustic Emissions"; Acta Oto-Laryngologica; 2015; pp. 758-764.

Mehta et al., "Measuring Serum Levels of the Inner Ear Protein, Prestin, in Asummetric Sensorineural Hearing Loss"; SSNHL Abstract; AAO, 1 page (2019).

Mukherjea, et al.; "Early Investigational Drugs for Hearing Loss"; Expert Opin Investigative Drugs; Feb. 2015; vol. 24, No. 2, pp. 201-217.

Parham, et al.; "Noise-Induced Trauma Produces a Temporal Pattern of Change in Blood Levels of the Outer Hair Cell Biomarker Prestin"; Hearing Research; 2019; vol. 371, pp. 98-104.

Park, et al.; "Short-Term Changes of Hearing and Distortion Product Otoacoustic Emissions in Sudden Sensorineural Hearing Loss"; Otology & Neurology; 2010; vol. 31, pp. 862-866.

Rybak, et al.; "Ototoxicity"; Kidney International; 2007; vol. 72, pp. 931-935.

Yang, et al.; "Age-Related Hearing Impairment and the Triad of Acquired Hearing Loss"; Cellular Neuroscience; 2015; vol. 9, Article 276, 12 pages.

Zheng, et al.; "Identification of Differentially Expressed cDNA Clones from Gerbil Cochlear Outer Hair Cells"; Audiology & Neuro-Otology; 2002; vol. 7, pp. 277-288.

* cited by examiner

DIAGNOSTIC REAGENTS AND METHODS SPECIFIC TO INNER EAR DISORDERS

CROSS-REFERENCE TO RELATED APPLICATIONS

This application claims priority to U.S. Provisional Application 62/117,220 filed on Feb. 17, 2015, which is incorporated herein by reference in its entirety.

FIELD OF THE DISCLOSURE

The present disclosure is related to compositions and methods for the diagnosis and treatment of inner ear disorders.

BACKGROUND

Inner ear disorders such as hearing loss and vertigo are common conditions that affect health and quality of life. The World Health Organization estimates that 5% of the world's population—360 million people—has disabling hearing loss. Almost 50 million Americans have hearing loss, including 1 in 5 teenagers. 60% of veterans returning from Iraq and Afghanistan come home with hearing loss and tinnitus, making hearing complaints, the number one war wound. Tinnitus affects 20% of Americans and hearing loss occurs in 90% of these cases. Hearing loss becomes more prevalent with age and those with even mild hearing loss are twice as likely to develop dementia. As a result, hearing loss is a common source of morbidity which deleteriously affects the ability to communicate. At present, audiometric testing is used for the diagnosis of hearing loss. However, early detection—i.e., before hearing loss becomes measurable by audiometric assessment or disabling—has the potential to prevent progression and substantially reduce a major burden on the society.

There are several inner ear disorders that result in vertigo. For example, benign paroxysmal positional vertigo (BPPV) can occur throughout the lifespan, from childhood into old age. It is believed to be the most common cause of dizziness. The one-year prevalence of individuals with BPPV attacks (new-onset and recurrent) rises steeply with age: from 0.5% in 18 to 39 year olds, to 3.4% in individuals over 60 years of age and the cumulative (lifetime) incidence of BPPV reaches almost 10% by the age of 80. Women are two times more likely to suffer from BPPV. Patients with BPPV are more likely to have depression, reduced activities of daily living scores and sustained a fall. Unfortunately, BPPV has a low recognition rate in the primary care setting and emergency rooms where patients with this disorder initially present. In consecutive examinations of 100 older patients in an urban clinic, 9% were found to have undiagnosed BPPV.

What is needed are compositions and methods suitable for early detection and diagnosis of inner ear disorders such as hearing loss and BPPV.

BRIEF SUMMARY

In one aspect, a method of detecting an inner ear disorder in a subject comprises providing a serum or plasma sample from the subject; determining a level of otolin-1, prestin, otoconin-90, oncomodulin, or a combination comprising two or more of the foregoing, in the serum or plasma sample from the subject; and determining that the subject is likely to have an inner ear disorder
when the level of otolin-1 in the serum or plasma sample is increased compared to a reference otolin-1 level,
when the level of otolin-1 in the serum or plasma sample is comparable to a level of otolin-1 of a reference population known to have an inner ear disorder,
when the level of prestin in the serum or plasma sample is decreased or increased compared to a reference prestin level,
when the level of prestin in the serum or plasma sample is comparable to a level of prestin of a reference population known to have an inner ear disorder,
when the level of otoconin-90 in the serum or plasma sample is decreased or increased compared to a reference otoconin-90 level,
when the level of otoconin-90 in the serum or plasma sample is comparable to a level of otoconin-90 of a reference population known to have an inner ear disorder,
when the level of oncomodulin in the serum or plasma sample is decreased or increased compared to a reference oncomodulin level,
when the level of oncomodulin in the serum or plasma sample is comparable to a level of oncomodulin of a reference population known to have an inner ear disorder, or
a combination thereof.

In another aspect, a method of detecting loss of hearing in a subject suspected of exposure to injurious levels of noise or an ototoxin comprises providing a first serum or plasma sample from the subject; determining a level of otolin-1, prestin, otoconin-90, oncomodulin, or a combination comprising two or more of the foregoing, in the first serum or plasma sample from the subject; exposing the subject to the injurious levels of noise, an ototoxin, head trauma or a viral illness; providing a second serum or plasma sample from the subject taken after the exposing; determining a level of otolin-1, prestin, otoconin-90, oncomodulin, or a combination comprising two or more of the foregoing, in the second serum or plasma sample from the subject; and determining that the subject is likely to have an inner ear disorder
when the level of otolin-1 is increased in the second serum or plasma sample compared to the first serum or plasma sample,
when the level of prestin is increased or decreased in the second serum or plasma sample compared to the first serum or plasma sample,
when the level of otoconin-90 is increased or decreased in the second serum or plasma sample compared to the first serum or plasma sample,
when the level of oncomodulin is increased or decreased in the second serum or plasma sample compared to the first serum or plasma sample, or
a combination thereof.

In yet another aspect, a kit comprises two or more of a specific anti-otolin-1 antibody, a specific anti-prestin antibody, a specific anti-otoconin-90 antibody, and a specific anti-oncomodulin antibody; and reagents for performing an immunoassay.

Figure 1:
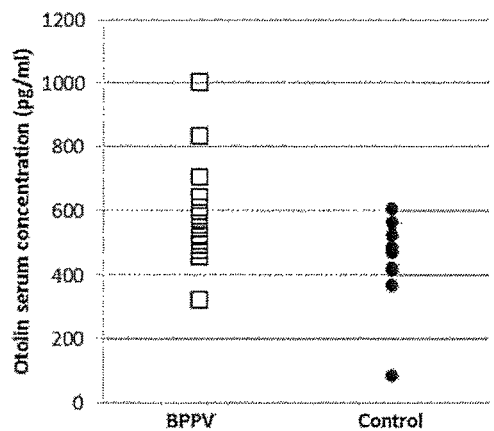
FIG. 1 shows serum otolin-1 concentration for subjects with benign paroxysmal positional vertigo (BPPV) and control subjects. BPPV subjects have higher otolin-1 concentrations in the circulation.

The above-described and other features will be appreciated and understood by those skilled in the art from the following detailed description, drawings, and appended claims.

DETAILED DESCRIPTION

Disclosed herein are methods for detecting inner ear disorders in subjects, including human subjects, comprising measuring biomarkers for inner ear disorders in samples from subjects such as serum or plasma samples. Biomarkers for inner ear disorders include otolin-1 and prestin as well as otoconin-90 and oncomodulin. Biomarkers help increase the accuracy of diagnosis, characterize disease, aid prognosis, predict response to treatment and guide treatment. Lack of serum biomarkers has been an impediment to early diagnosis and management of inner ear disorders (e.g., noise-induced and sudden sensorineural hearing loss, Meniere's disease, ototoxicity, and the like). Early detection of inner ear disorders using serum biomarkers will allow for the detection of these disorders before hearing loss is measureable by audiometric assessment, for example. Early identification of individuals at risk of hearing loss will allow intervention before development of disabling hearing loss and tinnitus and substantially reduce morbidity in potential sufferers and financial burden on society.

In an aspect, a method of detecting an inner ear disorder in a subject comprises providing a serum or plasma sample from the subject; determining a level of otolin-1, prestin, otoconin-90, oncomodulin, or a combination comprising two or more of the foregoing, in the serum or plasma sample from the subject; and determining that the subject is likely to have an inner ear disorder when the level of otolin-1 in the serum or plasma sample is increased compared to a reference otolin-1 level, when the level of otolin-1 in the serum or plasma sample is comparable to a level of otolin-1 of a reference population known to have an inner ear disorder, when the level of prestin in the serum or plasma sample is decreased or increased compared to a reference prestin level, when the level of prestin in the serum or plasma sample is comparable to a level of prestin of a reference population known to have an inner ear disorder, when the level of otoconin-90 in the serum or plasma sample is decreased or increased compared to a reference otoconin-90 level, when the level of otoconin-90 in the serum or plasma sample is comparable to a level of otoconin-90 of a reference population known to have an inner ear disorder, when the level of oncomodulin in the serum or plasma sample is decreased or increased compared to a reference oncomodulin level, when the level of oncomodulin in the serum or plasma sample is comparable to a level of oncomodulin of a reference population known to have an inner ear disorder, or a combination thereof.

As used herein, the term inner ear disorder includes balance disorders, and hearing disorders. Etiologies of hearing loss are diverse and can be broadly classified as congenital or acquired. Without being held to theory, it is believed that different ototoxins, as well as acoustic trauma, share common pathways leading to damage and death of cochlear sensory cells through activation of reactive oxygen species. Outer hair cells (OHCs) are susceptible to damage and are affected gradually from the base of the cochlea to its apex, producing a pattern of hearing loss that begins in high frequencies and progresses to lower frequencies. Inner hair cells are the sensory mechanoreceptor responsible for encoding sound wave-induced deflections of the basilar membrane. OHCs, on the other hand, are effector cells that enhance tuning and sensitivity of the cochlea. Without being held to theory, it is believed that since OHCs are early targets for noise-induced damage and ototoxins, measures related to OHCs should be sensitive early indicators of hearing loss. Based on the characteristics of OHCs, serum measurement of biomarkers specific to OHCs will allow the detection of inner ear disorders.

As used herein, the term inner ear disorder includes balance disorders such as benign paroxysmal positional vertigo (BPPV); hearing disorders such as tinnitus, acquired sensorineural hearing loss, high-frequency hearing loss, noise-induced hearing loss, blast induced hearing loss, or hearing loss induced by an ototoxin; acoustic injury; congenital hearing loss and other inner ear disorders.

Balance disorders include benign paroxysmal positional vertigo (BPPV), labyrinthitis, labyrinthine infarction, Meneire's disease, vestibular neuronitis, perilymph fistula, bilateral vestibular hypofunction, migraine-associated vertigo, and Mal de Debarquement Syndrome.

BPPV is the most common cause of dizziness. The majority of cases of BPPV are idiopathic (iBPPV). The current management strategy involving canalith repositioning fails to relieve symptoms in 20-30% of patients and does not address prevention of recurrent episodes. BPPV occurs at any age, but is more severe in geriatric populations, increasing the risk for falls and associated morbidities and consequently resulting in a decreased quality of life. It is a common problem that ER physicians who are not trained in administering a battery of detailed neurological tests, have a hard time distinguishing BPPV from a more serious emergency condition like a stroke. Therefore, many such patients get CT scans or MRIs who do not need such expensive imaging procedures. This type of situation represents one example of an unmet need that may be filled by the disclosed methods.

Additional inner ear disorders include acoustic neuroma, autoimmune inner ear disease, otosclerosis, infections such as meningitis, chronic otitis media, and the like.

Ototoxins are drugs or chemicals that cause damage to the inner ear resulting in hearing loss. Exemplary ototoxins include antibiotics such as gentamycin, streptomycin and tobramycin; anti-cancer drugs such as cisplatin, bleomycin and vincristine; diuretics such as acetazolamide, furosemide, bumetanide and ethacrynic acid; and antimalarial drugs such as quinine and chloroquine. Environmental chemicals that cause inner ear damage include tin, lead, mercury, carbon monoxide and carbon disulfide. Ototoxic solvents include trichloroethylene, xylene, toluene and hexane. Aspirin is also a known ototoxin.

Congenital hearing loss is associated with a variety of syndromes such as Alport syndrome, branchio-oto renal syndrome, x-linked Charcot Marie Tooth, Goldenhar's syndrome, Jervell and Lange-Nielsen Syndrome, Mohr-Tranebjaerg syndrome (DFN-1), Norrie Disease, Pendred Syndrome, Stickler syndrome, Treacher Collins syndrome, Waardenburg Syndrome and Usher syndrome.

As used herein, the term subject includes non-mammalian and mammalian species, specifically mammalian species such as humans. In certain aspects, the subject is not experiencing detectable injury or damage to the cochlea. In another aspect, the subject does not exhibit hearing loss as measured by audiogram.

Specific subjects include patients undergoing chemotherapy for cancer treatment, including pediatric patients, subjects exposed to noise-induced hearing loss in the military, and subjects exposed to noise or ototoxins in an occupational setting.

As used herein, samples include blood samples, specifically serum and plasma samples. Unlike whole blood, both plasma and serum samples do not contain blood cells. Serum is similar to plasma, however, in a serum sample, the blood clotting factors have been removed. In one aspect, providing a serum or plasma sample from the subject comprises providing a blood sample from the subject and isolating serum or plasma from the blood sample to obtain the serum or plasma sample.

In one aspect, the biomarker for inner ear disorders is otolin-1, a 70 kDa protein. The UniProt accession number for human otolin-1 is A6NHN0 (SEQ ID NO: 1). Otolin-1 is a secreted glycoprotein whose mRNA expression is restricted to the inner ear, specifically the support cells of the vestibular maculae, semicircular canal cristae, organ of Corti and marginal cells of the stria vascularis. Otolin-1 forms the scaffolding on which the organic and inorganic matrix of the otoconia form, and also forms the fibrils that interconnect the otoconia. The functions of otolin-1 include interaction with other specialized inner ear proteins, such as otoconin-90, to form and maintain otoconia.

As demonstrated herein, the inner ear scaffolding protein, otolin-1 can be detected and quantified in serum. Furthermore, the otolin-1 levels are higher in patients with BPPV than control subjects. Since otolin-1 can be measured in serum and current evidence suggests its expression is specific to the inner ear, it serves as a biomarker to diagnose and monitor inner ear disorders. Without being held to theory, detection of otolin-1 in serum is important because it demonstrates that this inner ear protein can exit the endolymph, pass through the labyrinth-blood barrier, and enter the systemic circulation.

In another aspect, the biomarker for inner ear disorders is prestin, an 80 kDa protein specifically expressed in OHCs. The UniProt accession number for human prestin is P58743 (SEQ ID NO: 2). Prestin is a protein localized to the lateral plasma membrane of outer hair cells, where electromotility occurs. Electromotility is believed to be the physical process that underlies the cochlear amplifier, thus prestin plays a central role in cochlear sensitivity and tuning. Outer hair cell and stria vascularis damage are two of the earliest events that lead to hearing loss from a number of different processes such as noise-induced hearing loss and ototoxicity. Apoptosis of these cellular targets is followed by phagocytosis by supporting cells and release of cellular contents, including structural proteins into circulation. Therefore, proteins such as prestin and also otolin-1 are uniquely suited for serving as biomarkers of inner ear function.

In rats exposed to intense noise, a statistically significant decrease in prestin levels compared to control animals was observed. In mice and rats exposed to the ototoxin cisplatin, serum concentrations of prestin increased with exposure to cisplatin.

Without being held to theory, it is believed that a time course in the change of serum prestin levels reflects the dynamic changes in the inner ear after exposure to injurious noise or ototoxins, for example. Because of inherent homeostatic cellular processes, baseline detection of prestin is expected at low levels. Within hours of hair cell damage from exposure to noise or ototoxins, prestin levels are expected to rise above baseline. About 3 to 5 days after exposure to the injurious process prestin levels are likely to peak and then decline, however, because of increased expression in the surviving OHCs, levels are expected to remain above baseline for at least 1 month after exposure if damage is mild. However, if damage is moderate to severe prestin levels will drop below baseline.

In another aspect, the biomarker for inner ear disorders is otoconin-90, a 90 kDa protein. Otoconin-90 is the principal matrix molecule of otoconia. The accession number for human otoconin-90 is Q02509 (SEQ ID NO: 3). Otoconin-90 interacts with other specialized inner ear proteins, such as otolin-1, to form and maintain otoconia. Thus it follows that when otoconia are resorbed, as would happen in BPPV, both otolin-1 and otoconin-90 would be released into circulation where they can be measured as we have demonstrated for otolin-1.

In another aspect, the biomarker for inner ear disorders is oncomodulin, a 12 kDa protein which in the inner ear is exclusively expressed in OHCs. The Uniprot accession number for human oncomodulin is P0CE72 (SEQ ID NO: 4). Although oncomodulin expression is not exclusive to the inner ear, because of its concentration in the OHCs, any damage to the OHC would result in release of its cellular building blocks into circulation, as we have demonstrated with prestin. Therefore, we would expect a rise relative to baseline in concentration of oncomodulin in circulation.

The level of otolin-1, prestin, otoconin-90 or oncomodulin in the sample can be determined by contacting the serum or plasma sample with an agent that specifically binds otolin-1, prestin, otoconin-90 or oncomodulin such as an antibody. Anti-otolin-1, anti-prestin, anti-otoconin-90 and anti-oncomodulin antibodies are commercially available. In one aspect, the assay is an immunoassay. Techniques for detection of a biomarker protein in a serum or plasma sample include enzyme linked immunosorbent assays (ELISAs), Western blots such as quantitative western blotting, immunoprecipitations, radioimmunoassays, immunofluorescence, immunochromotographic assays and flow cytometry assays.

Lateral flow test strips, or simply strip tests, are immunoassays for detecting various analytes of interest, are known in the art. The benefits of lateral flow tests include a user-friendly format, rapid results, long-term stability over a wide range of climates, and relatively low cost to manufacture. These features make lateral flow tests ideal for applications involving home testing, rapid point of care testing, and testing in the field for various analytes. Essentially, any ligand that can be bound to a visually detectable solid support, such as dyed microspheres, can be tested for, qualitatively, and semi-quantitatively.

In one aspect, it is determined that the subject is likely to have an inner ear disorder when the level of otolin-1 is increased compared to a reference otolin-1 level. Reference otolin-1 levels can be a baseline level from the subject or reference otolin-1 levels can be determined from a reference population that is not suffering from an inner ear disorder. A baseline level of otolin-1 in the subject can be prior to exposure to noise or an ototoxin, an inner ear injury, head trauma or viral illness, for example, or can be a measurement taken at an earlier point in time, such as one month, 6 months or a year or more prior to the current measurement. Alternatively, it is determined that the subject is likely to have an inner ear disorder when the level of otolin-1 is comparable to that of a reference population known to have an inner ear disorder.

In one aspect, it is determined that the subject is likely to have an inner ear disorder when the level of prestin is increased or decreased compared to a reference prestin level. Reference prestin levels can be a baseline level from the subject, or reference prestin levels can be determined from a reference population that is not suffering from an inner ear disorder. A baseline level of prestin in the subject can be prior to exposure to noise or an ototoxin, an inner ear injury, head trauma or viral illness, for example, or can be a measurement taken at an earlier point in time, such as one month, 6 months or a year or more prior to the current measurement. Alternatively, it is determined that the subject is likely to have an inner ear disorder when the level of prestin is comparable to that of a reference population known to have an inner ear disorder.

In another aspect, it is determined that the subject is likely to have an inner ear disorder when the level of otoconin-90 is increased or decreased compared to a reference otoconin-90 level. Reference otoconin-90 levels can be a baseline level from the subject, or reference otoconin-90 levels can be determined from a reference population that is not suffering from an inner ear disorder. A baseline level of otoconin-90 in the subject can be prior to exposure to noise or an ototoxin, an inner ear injury, head trauma or viral illness, for example, or can be a measurement taken at an earlier point in time, such as one month, 6 months or a year or more prior to the current measurement. Alternatively, it is determined that the subject is likely to have an inner ear disorder when the level of otoconin-90 is comparable to that of a reference population known to have an inner ear disorder.

In yet another aspect, it is determined that the subject is likely to have an inner ear disorder when the level of oncomodulin is increased or decreased compared to a reference oncomodulin level. Reference oncomodulin levels can be a baseline level from the subject, or reference oncomodulin levels can be determined from a reference population that is not suffering from an inner ear disorder. A baseline level of oncomodulin in the subject can be prior to exposure to noise or an ototoxin, an inner ear injury, head trauma or viral illness, for example, or can be a measurement taken at an earlier point in time, such as one month, 6 months or a year or more prior to the current measurement. Alternatively, it is determined that the subject is likely to have an inner ear disorder when the level of oncomodulin is comparable to that of a reference population known to have an inner ear disorder.

As used herein, increased means a statistically significant increase, such as a p-value of greater than 0.05. As used herein, decreased means a statistically significant decrease, such as a p-value of greater than 0.05. Alternatively, an increase or decrease could be compared to 95% confidence interval for normal reference range. A statistically significant increase can be an increase of 20% compared to a reference. A statistically significant decrease can be decrease of 20% compared to a reference A reference population that is not suffering from an inner ear disorder can include healthy subjects, such as 50 to 100 subjects for example, and can be an age-matched (within 10 years) sample e.g., 1-20, 20-40, 40-60, 60-80 and 80+. Such a population should have no significant past history of exposure to ototoxic agents, damaging noise or infection If it is determined, based on the otolin-1, prestin, otoconin-90, or oncomodulin levels, that the subject has an inner ear disorder, the method may further comprise measuring pure tone audiometry, an auditory brainstem evoked response (ABR) threshold, a distortion product otoacoustic emission (DPOAE) level, or a combination thereof in the subject. Audiometry is a behavioral technique for assessing hearing. The ABR threshold and the DPOAE levels are electrophysiological measures of hearing that can, for example, detect disruption of hearing function.

In another embodiment, if it is determined using pure tone audiometry, an auditory brainstem evoked response (ABR) threshold, a distortion product otoacoustic emission (DPOAE) level, or a combination thereof in the subject that the subject suffers from hearing loss, one may then measure the levels of the otolin-1, prestin, otoconin-90, and/or oncomodulin in a serum or plasma sample from the subject. The measurement of biomarkers for hearing loss can be used as an adjunct to electrophysiological measures of hearing.

In another aspect, a method of detecting loss of hearing in a subject suspected of exposure to injurious levels of noise or an ototoxin comprises, providing a first serum or plasma sample from the subject;
determining the level of otolin-1, prestin, otoconin-90, oncomodulin, or a combination comprising two or more of the foregoing, in the first serum or plasma sample from the subject;
exposing the subject to the injurious levels of noise, an ototoxin, head trauma or a viral illness;
providing a second serum or plasma sample from the subject taken after the exposing; determining the level of otolin-1, prestin, otoconin-90, oncomodulin, or a combination comprising two or more of the foregoing, in the second serum or plasma sample from the subject; and
determining that the subject is likely to have an inner ear disorder
when the level of otolin-1 is increased in the second serum or plasma sample compared to the first serum or plasma sample,
when the level of prestin is increased or decreased in the second serum or plasma sample compared to the first serum or plasma sample,
when the level of otoconin-90 is increased or decreased in the second serum or plasma sample compared to the first serum or plasma sample,
when the level of oncomodulin is increased or decreased in the second serum or plasma sample compared to the first serum or plasma sample, or
a combination thereof.

In certain embodiments, the level of otolin-1, prestin, otoconin-90, oncomodulin, or a combination comprising two or more of the foregoing is determined after exposure to injurious noise or an ototoxin. Measurements within one to three days would permit assessment of acute changes in otolin-1, prestin, otoconin-90, oncomodulin, or a combination comprising two or more of the above. Acute measurements within days (from one to seven) will reflect ongoing damage/resorption producing increase relative to a reference range. In contrast, subacute measurements within weeks (from two or more weeks) demonstrate a decrease relative to reference range, reflecting cochlear status.

It is widely believed that displacement of otoconia (calcium carbonate crystals) from the macula of the utricle into the semicircular canals and ampulla of the semicircular canals (canalithiasis and cupulolithiasis, respectively) underlies BPPV. The displaced otoliths can induce endolymph flow on head movement or convert structures sensitive to angular acceleration to linear/gravitational detectors. As a result, changes in head position (e.g., getting out of bed or standing up from a seated position) produce brief periods of vertigo and nystagmus which can precipitate nausea, imbalance and falls. The data provided herein suggest that otoconia matrix proteins can be detected in the serum.

Further included herein is a kit for detecting an inner ear disorder, the kit comprising two or more of a specific anti-otolin-1 antibody, a specific anti-prestin antibody, a specific anti-otoconin-90 antibody, and a specific anti-oncomodulin antibody. In certain aspects the kit also includes instructions for use. In other aspects, the kit includes reagents for performing an immunoassay such as buffers and detection antibodies as well as a support for performing the immunoassay. The kit optionally further comprises a reagent for determining the level of a bone turnover marker.

The invention is further illustrated by the following non-limiting examples.

EXAMPLES

Methods
Method of Screening for Biomarkers of Otologic Disorders

Serum samples from 14 postmenopausal women with a history of posterior canal benign paroxysmal positional vertigo (BPPV) and 10 postmenopausal women who had no history of otologic disorders were used. This approach allowed the inventors to keep the subject population uniform and limit confounding effects of sex and hormonal influences. Additional information on subjects and procedural details for verification of diagnoses are known in the art.

Morning fasting blood samples were collected from all subjects. Collected specimens were allowed to clot and spun at 3000 rpm for 15 minutes at 4° C. Serum was then removed and frozen at −80° C. until time of assay. Otolin-1 was measured in the serum using the Human-OTOL1 enzyme-linked immunosorbent assay (ELISA) kit (QAYEEBIO, Atlanta, Ga.) as described in the manufacturer's instruction manual. A 1:5 dilution was prepared, and each serum sample was assayed in triplicate. The optical density in the wells of the ELISA microplate was measured at 450 nm using a BioTek® ELx808 plate reader, and data were compiled using the KCJunior™ software package (BioTek® Instruments, Winooski, Vt.).

Method of Validation of Otolin-1 as a Serum Biomarker of BPPV

Subjects: Study procedures were carried out in accordance with the ethical standards of the Institutional Review Board and with the Helsinki Declaration on human experimentation. Postmenopausal women with a diagnosis of BPPV within the prior 3 years were recruited from the Division of Otolaryngology—Head and Neck Surgery patient base, and women with a history of osteopenia or osteoporosis were recruited from the Osteoporosis Clinic patient base. Bone turnover markers and serum otolin-1 levels among these subjects were previously analyzed. The inclusion criterion in the present study was a positive Dix-Hallpike test. Exclusion criteria included the inability to consent, cranial neuropathies, vulnerable populations (e.g., trainees and prisoners), any history of non-BPPV vestibular diagnoses or previous ear operations, any history of balance disorders of other etiology, the presence of otitis media, the inability to undergo positional testing, and an incomplete data set. Thirteen women met the inclusion criteria for this study and were included.

Clinical diagnosis of BPPV: A diagnosis of BPPV was ascertained with a suggestive history and an otherwise benign physical examination combined with confirmatory positional testing. Histories obtained as indicative of this diagnosis were those noting intermittent and brief vertiginous episodes occurring secondary to changes in head position without additional otologic complaints. Patients then underwent examinations to confirm normal cranial nerve function and otoscopy. Finally, a Dix-Hallpike test utilizing Frenzel goggles identified nystagmus consistent with posterior canal BPPV in all patients (torsional upbeat, geotropic with gaze straight ahead).

Data collection: Morning fasting blood samples were obtained. Serum otolin-1, as a marker of otoconia resorption, was measured using the Human-OTOL1 ELISA kit (QAYEE-BIO, Atlanta, Ga., U.S.A.). Additional samples were obtained for measurement of ionized calcium (iCa); 25-hydroxy vitamin D (IDS; distributed in the US by Immunodiagnostic Systems Limited, Fountain Hills, Ariz., U.S.A.); a marker for bone resorption, aminoterminal telopeptides of collagen (NTX) (Wampole Labs, Princeton, N.J., U.S.A.); and a marker for bone formation, aminoterminal propeptide of protocollagen type I (P1NP) (Orion Diagnostica, Espoo, Finland). Vitamin D levels were reported in nmol/L which can be divided by 2.5 to convert into ng/ml. The normal range for vitamin D level was >75 nmol/L. Vitamin D insufficiency was defined as a level between 50 and 75 nmol/L and vitamin D deficiency being <50 nmol/L. Normal ionized calcium range was defined as 1.14 to 1.33 mmol/L. The lowest T-score obtained on DEXA scans of the proximal femur or lumbar spine was used to define bone mass density. A T-score less than −1 was defined as abnormal (between −1 and −2.5 osteopenia; −2.5 or less osteoporosis).

Statistical Analysis: Two-tailed bivariate correlation analysis between various variables was carried out by calculating Pearson's r using IBM SPSS Statistics V22. The alpha for statistical significance was 0.05. The value of Pearson's r was categorized using "rule of thumb" based on:

+0.70 or higher Very strong positive relationship
+0.40 to +0.69 Strong positive relationship
+0.30 to +0.39 Moderate positive relationship
+0.20 to +0.29 weak positive relationship
+0.01 to +0.19 No or negligible relationship
−0.01 to −0.19 No or negligible relationship
−0.20 to −0.29 weak negative relationship
−0.30 to −0.39 Moderate negative relationship
−0.40 to −0.69 Strong negative relationship
−0.70 or higher Very strong negative relationship Method of Validation of Prestin as a Cochlear Biomarker Subjects: 27 male Wistar rats were used in this study (4 speaker/121/2; Noise: 21 ABR/20DPOAE; 6 control). The rats were 6-11 weeks of age at sampling. Rats were provided ad lib access to food and water and housed in 12 hour light-dark cycle.

Noise exposure: Noise trauma was induced with exposure to loud (115-121 dB) octave band of noise (8-16 kHz) for 2-3 hours. This octave band corresponds to a distance of 40-56% distance from the apex (44-60% distance from the base of the cochlea).

Anesthesia: The distortion product otoacoustic emissions (DPOAE) and auditory brainstem response (ABR) stimuli were presented and response waveforms collected using a Tucker-Davis Auditory Workstation. Stimuli were delivered through MF-1 speakers. Emissions were recorded using an Etymotic ER-10B+. The F1 and F2 DPOAE stimulus frequencies (F2/F1=1.2) were selected such that their geometric means were 4, 8, 16, 24 and 32 kHz. Stimulus levels were L1=z and L2=y. The 2F1-F2 DPOAE were measured. For ABRs tone bursts (x msec duration, y msec rise-fall time) at 8, 16 and 24 kHz were used. Stimuli were delivered in 5 dB steps between x-y dB SPL to determine the threshold (defined as the lowest SPL to elicits a wave III).

Example 1

Identification of Otolin-1 as an Otologic Biomarker

Figure 2:
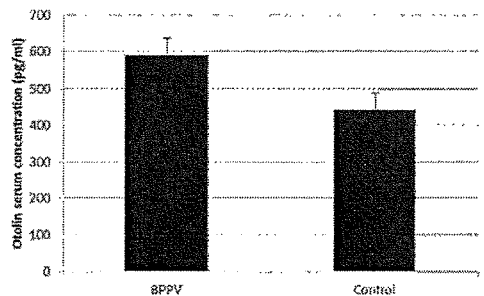
FIG. 2 shows a comparison of mean serum otolin-1 levels. Error bars represent SEM.

Otolin-1 was detected in the serum samples of all subjects. FIG. 1 shows the distribution of serum otolin-1 concentration for the 2 groups. In control subjects, otolin-1 levels ranged from 86.3 to 607 pg/mL, with an average of 443.1±45.2 (mean 6 SEM) pg/mL. Among subjects with BPPV, levels ranged from 324.7 to 1002.3 pg/mL, with an average concentration of 590±645 (mean 6 SEM) pg/mL. One third of subjects with BPPV had levels above the control range. On average, the BPPV group had higher serum levels by 150 pg/mL (FIG. 2). A 2-tailed t test demonstrated that the difference between the 2 groups was statistically significant (P=036).

Since otolin-1 can be measured in serum and current evidence suggests its expression is specific to the inner ear, serves as a biomarker to diagnose and monitor inner ear disorders. Detection of otolin-1 in serum is important because it proves that this inner ear protein can exit the endolymph, pass through the labyrinth-blood barrier, and enter the systemic circulation.

Benign paroxysmal positional vertigo (BPPV), which involves fragmentation of otoconia, is convenient for proof of concept because its diagnosis can be objectively verified using the Dix-Hallpike maneuver. Otolin-1 forms the scaffolding on which the organic and inorganic matrix of the otoconia forms, as well as the fibrils that interconnect the otoconia. From a practical perspective, otolin-1 levels may be used, for example, in up to 30% of BPPV cases where diagnosis and management is challenging (e.g., lateral, superior, or multiple/bilateral canal involvement).

Only one-third of subjects with BPPV had serum otolin-1 values above control range. The absence of 100% differentiation may reflect that subjects with BPPV had their sentinel/most recent episode up to 2 years prior to enrollment into the study.

Example 2

Correlation Between Otolin-1 and Bone Turnover Markers (BTMs)

Inner ear biomarkers can be used to explore relationship of inner ear disorders to other comorbidities. For example, the relationship between BTMs and otolin-1 has been explored. BTMs include procollagen type I N-terminal propeptide (P1NP) and the aminoterminal telopeptide of collagen type I (NTX). Other important determinants of bone turnover include calcium, and vitamin D,. P1NP and NTX represent biomarkers for osteopenia/osteoporosis.

Figure 3:
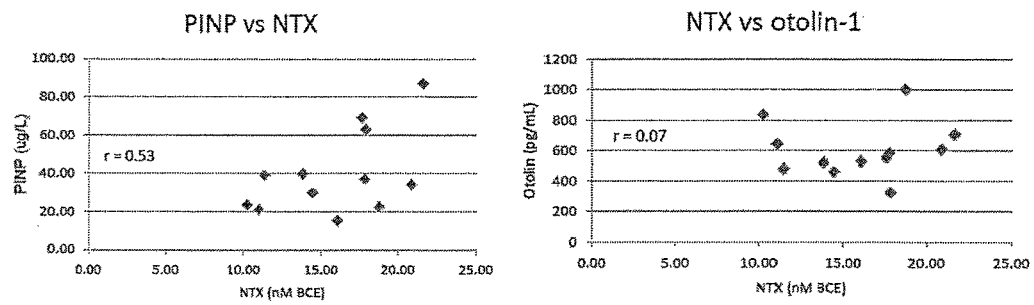
FIG. 3 shows scatter diagrams of the positive correlation between levels of bone turnover markers P1NP and NTX (left panel). There is no significant relationship between serum levels of turnover marker, NTX and otoconia matrix protein, otolin-1 (right panel). This figure illustrates how inner ear biomarkers can be used to investigate the relationship of inner ear disorders to other non-otologic disorders.

P1NP and NTX levels were strongly correlated (r=0.53), however, otolin-1 levels lacked a correlation with either marker (r=0.07, −0.22) (FIG. 3). There was a moderate positive correlation between otolin and vitamin D levels (r=0.43). These results suggest that the relationship between the two conditions may be complex and that vitamin D levels may influence BPPV. From a practical perspective, these findings question the prospects of preventing BPPV attacks/recurrences through treatment of associated osteoporosis, but warrant vitamin D consideration.

Example 3

Association Between BPPV and Osteoporosis

The subjects ranged in age from 52 to 81 years of age. Among the subjects, 85% had documented recurrent BPPV. In total, 88%, 82%, 18%, and 18% were being treated with vitamin D supplements, calcium, bisphosphonates, and hormone replacement therapy, respectively, at the time of serum sampling. Only two subjects (11.7%) were found to have below normal vitamin D levels (insufficiency to be specific). No subjects had hypocalcemia, whereas three subjects (18%) had mild hypercalcemia. In total, 70% had osteopenia or osteoporosis (T-score<−1).

Figure 4:
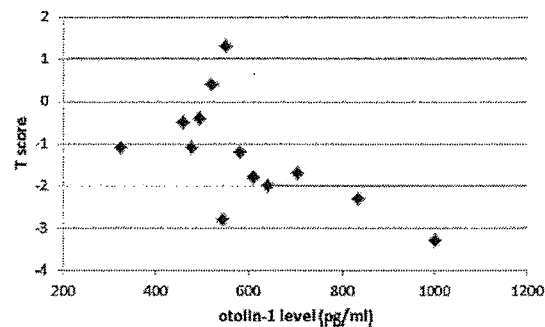
FIG. 4 shows the relationship of T-score and serum otolin-1 levels in the study of Example 3. This figure illustrates how inner ear biomarkers can be used to investigate the relationship of inner ear disorders to other non-otologic disorders, in this case osteopenia/osteoporosis.

Table 1 shows the results of the pairwise correlation analyses between all variables. As expected, there was a strong positive correlation between serum markers of bone turnover, P1NP and NTX (r=−0.65, p¼0.016). A strong correlation was observed between otolin-1 levels and subjects' T-scores (r=−0.6, p¼0.032). This relationship is illustrated in FIG. 4. Otolin-1 levels seemed to be higher in patients with lower T-scores, consistent with a strong negative relationship between the two variables. However, neither P1NP nor NTX had a strong relationship with otolin-1 (Table 1). Applying the rule of thumb to correlation analyses, several other strong relationships were identified. These included a strong negative relationship between vitamin D and T-score, ionized calcium and T-score, and age and NTX. However, these were not statistically significant.

TABLE 1

Pearson's r for pairwise comparisons

|  | Otolin-1 | T-score | Vit D | P1NP | NTX | iCa | Age |
|---|---|---|---|---|---|---|---|
| Otolin-1 | 1.00 | −0.6[a] | 0.38 | −0.32 | −0.02 | 0.07 | −0.43 |
| T-score | −0.6[a] | 1.00 | −0.53[b] | 0.26 | −0.01 | −0.51[c] | 0.42 |
| Vit D | 0.38 | −0.53[b] | 1.00 | −0.37 | 0.29 | 0.25 | −0.11 |
| P1NP | −0.32 | 0.26 | −0.37 | 1.00 | 0.65[d] | 0.28 | 0.48 |
| NTX | −0.02 | −0.01 | 0.29 | 0.65[d] | 1.00 | 0.22 | 0.55[e] |
| iCa | 0.07 | −0.51[c] | 0.25 | 0.28 | 0.22 | 1.00 | −0.04 |
| Age | −0.43 | 0.42 | −0.1 | 0.48 | 0.55[e] | −0.04 | 1.00 |

[a] p = 0.032;
[b] p = 0.064;
[c] p = 0.078;
[d] p = 0.016;
[e] p = 0.05.
Boldface identifies statistically significant correlations.
Vit D indicates vitamin D; P1NP, aminoterminal propeptide of protocollagen type 1; NTX, amino terminal telopeptides of collagen; iCa, ionized calcium.

The finding of a strong correlation between T-scores and serum otolin-1 levels further supports the association between BPPV and osteoporosis. However, one limitation of DEXA scan measurements is that it takes about 1 year of progressive physiological alterations in bone turnover before a change is detectable. Since osteoporosis is a slowly progressive disease process, there is an obvious temporal incongruence with BPPV episodes, which tend to present abruptly and are typically self-limited (days to weeks in duration). To overcome this limitation, the relationship between their respective serum markers was explored. Bone turnover markers are used to predict bone density changes and future fracture risk; identify patients with metabolic bone diseases; assess the efficiency of antiresorptive and/or anabolic therapies; as well as monitoring the response or compliance of patients to such therapies. The changes observed in levels of these markers are rapid (within 1-3 months) and are sufficiently sensitive to effectively monitor bone turnover. Thus, levels of biochemical markers are likely to be more sensitive measures for analyzing the association of bone turnover and BPPV. Our investigation showed no relationship between biomarkers of BPPV and those of bone formation or resorption. Without being held to theory, we interpret this as evidence that this relationship is complex but not causal. Also without being held to theory, there may be an association between vitamin D deficiency and recurrent BPPV.

Example 4

Effects of Noise Trauma on ABR Thresholds and DPOAE Levels

Figure 5:
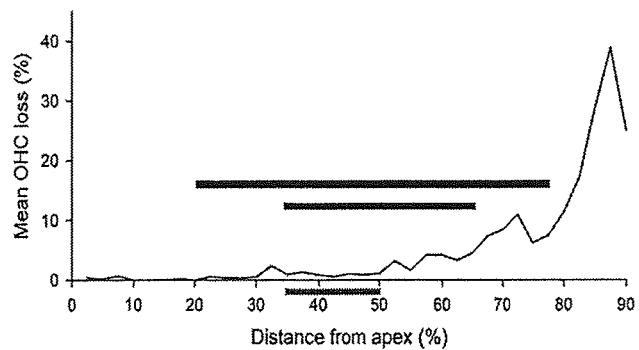
FIG. 5 shows the percent outer hair cell (OHC) loss as a function of distance from the apex of the cochlea 14 days after acoustic trauma. The lowest horizontal bar represents the approximate region corresponding to the octave band (8-16 kHz) used to induce trauma. Auditory brainstem response (ABR) (upper horizontal bar) measurements at 8-24 kHz represent a region from 40-70% distance from the apex. Distortion product otoacoustic emission (DPOAE) (middle horizontal bar) measurements at 4-32 kHz represent a region from 20-75% distance from the apex.

FIG. 5 shows a cochleogram depicting OHC loss as a function of distance from apex in noise exposed rats. The pattern of OHC loss showed up to 40% loss near the base with a rapid decline in hair cell loss toward the apex on Day 14. OHC loss was primarily basal to the region of the cochlea corresponding to the octave band of noise (FIG. 5, lowest bar). To assess the impact of these losses, DPOAE levels and ABR thresholds were measured in regions of the cochlea overlapping with the noise exposure, but principally extending basally.

Figure 6:
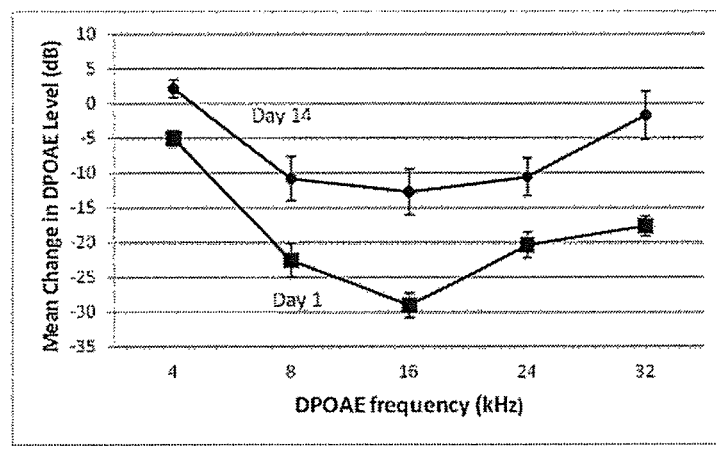
FIG. 6 shows the mean change in DPOAE as a function of stimulus frequency one and fourteen days after acoustic trauma. Error bars represent SEMs. This figure illustrates a functional measure from OHC loss shown in FIG. 5.

As expected, noise trauma induced changes in ABR thresholds and DPOAE levels. DPOAE levels were examined from 4-32 kHz, a three octave range covering approximately to 60% of cochlear length. FIG. 6 shows mean change in DPOAE levels one and 14 days after noise exposure. The 'DPOAE-gram' showed a maximum decrease in DPOAE level at 16 kHz with corresponding to the high-frequency limit of the noise band used to induce trauma. Temporary changes are depicted in the Day 1 results, whereas, Day 14 results likely represent permanent damage.

Figure 7:
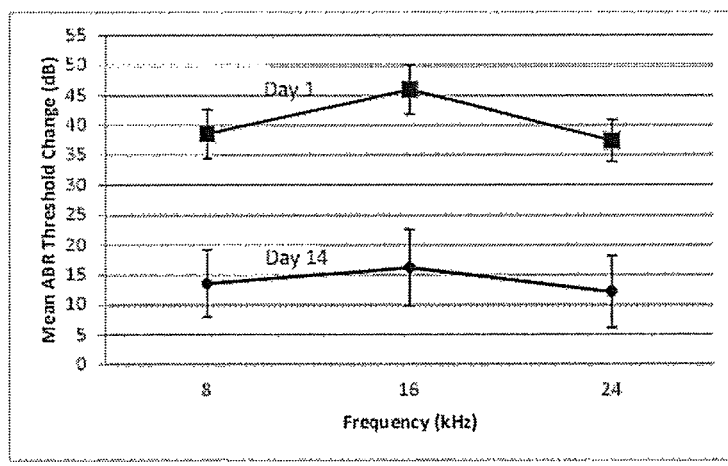
FIG. 7 shows the mean change in ABR threshold relative to baseline in noise exposed rats as a function of stimulus frequency one and fourteen days after acoustic trauma. Error bars represent SEMs. This figure illustrates another functional measure of inner ear damage shown in FIG. 5.

Whereas, DPOAE level is believed to be a more direct index of OHC function, ABR threshold reflects sensitivity of the system (i.e., inner and outer hair cells, neurons from spiral ganglion to midbrain). FIG. 7 shows ABR threshold change after noise trauma. ABR threshold rose sharply one day after trauma. On Day 1 after trauma, mean ABR threshold elevations ranged from 37-46 dB across the three frequencies tested. On Day 14, temporary threshold shifts had resolved leaving being ABR threshold elevations of 12-16 dB across frequencies without a significant statistical difference as a function of stimulus frequency (repeated measures ANOVA, p=0.6) (FIG. 7).

Figure 8:
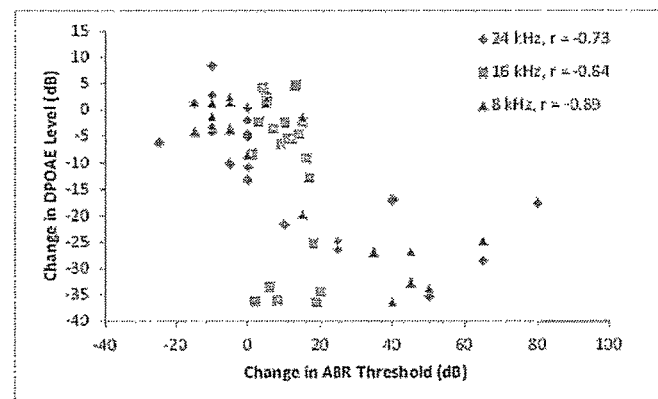
FIG. 8 shows the relationship of change in DPOAE level and change in ABR threshold fourteen days after acoustic trauma. Pearson correlation coefficients for 8, 16 and 24 kHz are shown in the inset. Functional measures of inner ear damage correlate well with one another.

The relationship between the change in DPOAE level and ABR threshold was negative, but strong and linear (FIG. 8). The slope of the best fit line for this relationship was much steeper at 16 kHz, than at either 8 or 24 kHz. These results suggest a strong influence of OHC function on ABR threshold 14 days after acoustic trauma.

Example 5

Prestin Levels in Noise-exposed Rats

Figure 9:
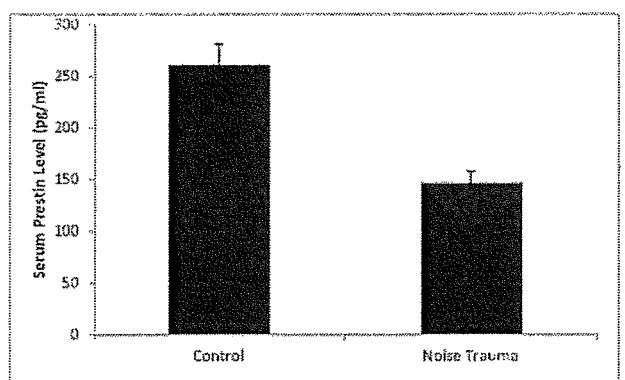
FIG. 9 shows the mean prestin concentrations of the control and noise-exposed rats fourteen days after trauma. Error bars represent SEMs. Noise-damaged animals had significantly lower levels of prestin.

FIG. 9 shows mean prestin concentrations in controls in comparison to noise-exposed rats. Prestin levels were 56% lower in the noise-exposed group. A one-tailed t-test showed this difference to be significant (p=0.0003).

Figure 10:
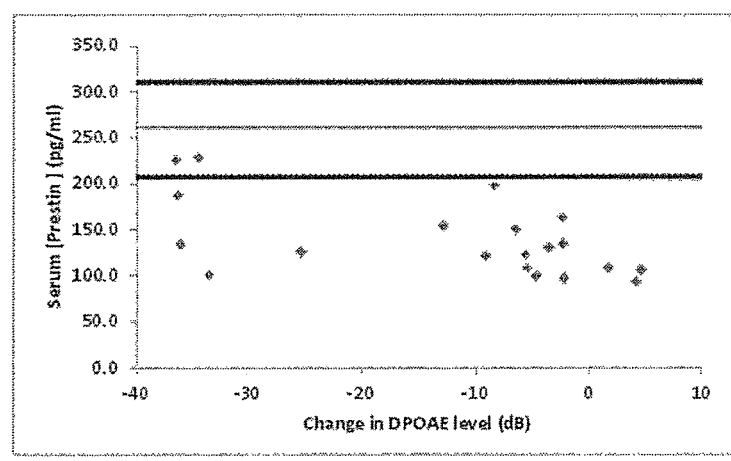
FIG. 10 shows the serum prestin concentration as a function of mean change in 16 kHz DPOAE level fourteen days after acoustic trauma. The middle horizontal line represents the mean serum prestin concentration in controls and the upper and lower horizontal lines illustrate the 95% CI intervals.
Figure 11:
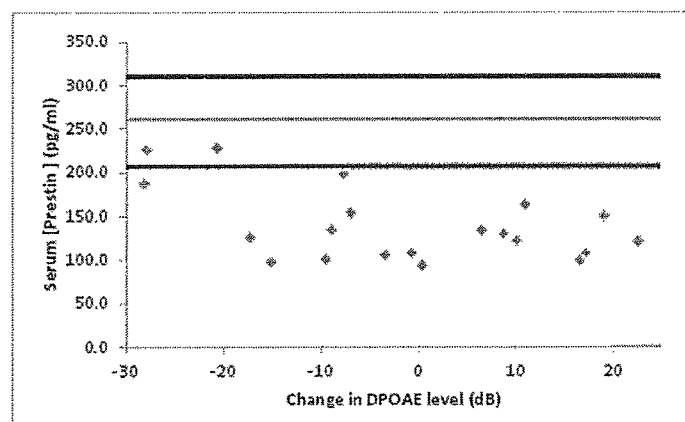
FIG. 11 shows the serum prestin concentration as a function of mean change in 32 kHz DPOAE level fourteen days after acoustic trauma. The middle horizontal line represents the mean serum prestin concentration in controls and the upper and lower horizontal lines illustrate the 95% CI intervals.

FIG. 10 shows the relationship of serum prestin concentration to the change in DPOAE level at 16 kHz, 14 days after noise trauma. There appears to be a clustering of DPOAE level change above −15 dB, with prestin concentrations being well below those of control rats. A second, smaller group, of rats had large changes in DPOAE level and a broader range of distribution of prestin concentrations, overlapping with the lower range of 95% CI of controls. Overall, there appeared to be a linear negative, relationship between serum prestin concentration and DPOAE level change (r=−0.563, p=0.01). Because the 'DPOAE-gram' showed a significant effect of stimulus frequency, the relationship of DPOAE level change to serum prestin concentrations at individual frequencies was studies as well as 5-tone average. The distributions showed little variation except at 32 kHz. The distribution of prestin concentrations as a function of change in DPOAE level is also shown for 32 kHz (FIG. 11). The notable difference relative to the 16 kHz distribution (FIG. 10) is the more even distribution of level changes, but the correlation between level change and prestin concentration remains strong (r=−0.51, p=0.02).

Figure 12:
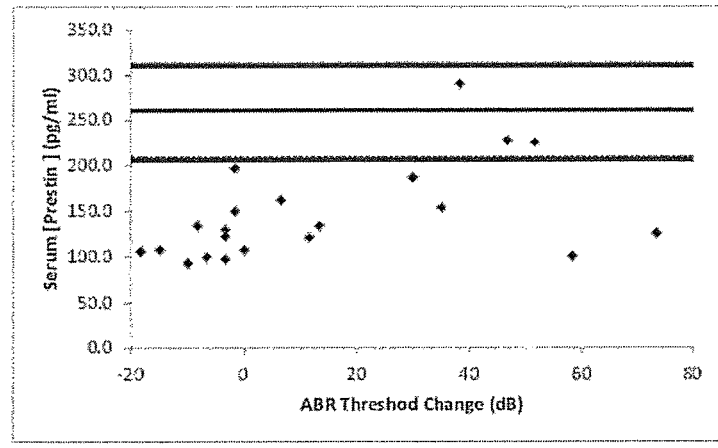
FIG. 12 shows the distribution of serum prestin concentration fourteen days after noise trauma as a function of 3-tone ABR threshold change. The middle horizontal line represents the mean serum prestin concentration in controls and the upper and lower horizontal lines illustrate the 95% CI intervals.

FIG. 12 shows the relationship of serum prestin concentration as a function of ABR threshold. There was little difference in the pattern of distribution as a function of stimulus frequency, therefore, 3-tone average is displayed. The majority (⅔) of the subjects displayed ABR thresholds which fluctuated within 20 dB of baseline. In these subjects, serum prestin concentration was decreased below 95% CI mean of the control subjects. There appeared to be a linear positive relationship between prestin concentration and ABR threshold change, such that prestin levels were substantially below normal when there were small threshold changes, but subjects which had threshold decreases greater than 40 dB, but less than 60 dB, could had near normal levels. In fact, although number of subjects in the latter range is small, they had either normal or slightly reduced prestin levels. Overall, the correlation was strong and statistically significant (r=0.46, p=0.36). If the two subjects with the highest threshold elevations (i.e., ≥60 dB) are excluded from the analysis, the strength of the correlation is further increased (r=0.80, p=0.0).

In summary, changes in both the functional measures of overall hearing capacity (ABR) and outer hair cell functional state (DPOAE) were associated with changes in circulating prestin concentrations. That is, after exposure, prestin concentrations in the serum were low when ABR thresholds and DPOAE levels changes showed small fluctuations around baseline (−20 to 20 dB and −10 to 10 dB, respectively), but there was a trend toward normal or mixed (normal or low) prestin concentrations when ABR threshold were elevated by more than 40 dB and DPOAE levels were decreased by more than 20 dB. These findings reflect the complexity of changes in the cochlea after exposure to injurious noise. Prestin concentration reflects specifically state of the OHCs (when decreased, injury or death), but by itself cannot inform on location of injury (e.g., basal or apical; right or left ear) or other damage (e.g., inner hair cell, neural, etc.). Therefore, the change in serum prestin level serves as a powerful indicator of OHC damage when there is little or no change in functional measures.

Two weeks after exposure to an injurious level of noise, prestin levels are significantly below that of unexposed control levels. These results provide proof of concept for a serum biomarker for inner ear damage and hearing loss. Our approach represents an entirely novel strategy in hearing diagnostics. For example, serum measurement of a biochemical marker of inner ear function can be used as an adjunctive approach to early detection of hearing loss. Until the experiments described herein were performed, no specific circulating biomarkers to diagnose, manage or investigate inner ear diseases had been utilized.

Currently, clinicians are heavily reliant on audiometric measurements, such as pure tone audiometry, otoacoustic emissions and evoked potentials for hearing loss. Although these diagnostic resources provide useful information, there still remain significant limitations in early detection of hearing loss. This is in part due to practical barriers in timely utilization of these tests which can be expensive, time consuming and require specialists to perform. These tests also have technological limitations in detecting damage before it actually produces hearing loss, by which time the degenerative cascades are in progress. Consequently, at present, early detection of inner ear pathology is not possible in high risk settings (e.g., patients undergoing chemotherapy for cancer treatment or noise-induced hearing loss in the military, leisure or occupational settings). Since outer hair cells (OHCs) are early targets for noise and ototoxins-induced damage, it has been proposed that functional measurement of OHC function should be a sensitive early indicator of hearing loss. Otoacoustic emissions, discovered in late 1970's are one such example whose measurements represent a clinical tool which specifically targets OHC function. However, due to a number of technical challenges in utilization of otoacoustic emissions, the promise of early detection of hearing loss in the clinical setting has yet to be realized.

The identification of prestin as a biomarker of hearing loss opens the door to detecting hearing loss at the earliest stages, when the damage is noticeable only on the micro-scale of OHC function, and potentially classify patients according to type of hearing loss in order to select optimal individualized treatments. The development of a serological assay would prevent deterioration and allow treatment before hearing is significantly and permanently impaired by ototoxic drugs and noise. In addition, identification of novel serum biomarkers for inner ear diseases will be helpful in development of novel therapeutics and in the stratification of patients based on hearing loss type to enable the development of personalized medicine approaches.

Example 6

Changes in Prestin Concentration in Mice Treated With Cisplatin

Figure 13:
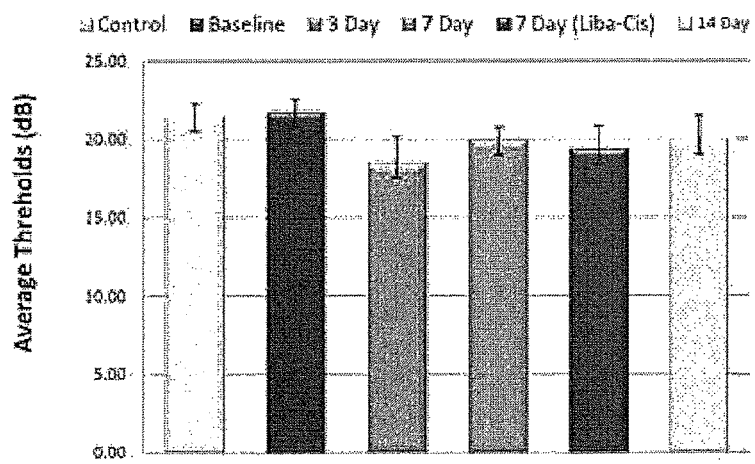
FIG. 13 shows an assessment of hearing using a standard testing protocol called click-evoked ABR in mice treated with cisplatin, an ototoxic drug. Mice are believed to be fairly resistant to ototoxic drugs. At this dose in mice, no significant measurable hearing loss could be demonstrated.
Figure 14:
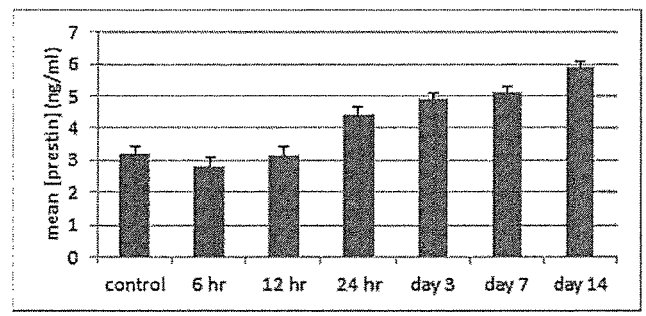
FIG. 14 shows serum concentrations of prestin over the same time course as FIG. 13. Although the hearing threshold measured by ABR was unaffected, prestin levels continued to change after exposure to cisplatin. This suggests that at least under some circumstances, a serum biomarker such as prestin has greater sensitivity in detecting inner ear damage than standard audiometric measures.

In this experiment, mice were treated with an ototoxic agent that demonstrates changes in a biomarker, prestin, for cochlea. The ototoxin drug cisplatin (a commonly used chemotherapeutic agent) was administered and then functional assessment of hearing and measurement of prestin were carried out at several intervals up to two weeks after exposure. Hearing was assessed using a standard testing protocol called click-evoked auditory brainstem response (ABR) (FIG. 13). In FIG. 13, ABR thresholds are shown as a function of time after administration of cisplatin. No significant change in ABR thresholds were detected, meaning that hearing threshold as measured by this method is unaffected. However, over the same time course, serum concentrations of prestin were found to be increasing (FIG. 14). This suggests that inner ear/cochlea is being affected by exposure to the ototoxin and that use of the biomarker prestin in serum can detect injury before the commonly used functional measure of hearing assessment can (i.e., detection of the biomarkers is more sensitive than the functional measurement of hearing).

Example 7

Changes in Prestin in Rats Treated with Cisplatin

Figure 15:
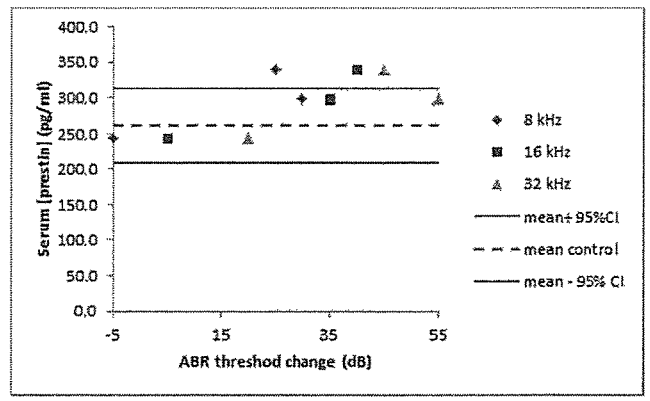
FIG. 15 shows an assessment of hearing using a standard testing protocol called tone-evoked auditory brainstem response in rats 72 hours after treatment with cisplatin. Rats are more sensitive to ototoxic drugs than mice and therefore exhibit significant hearing loss. Also shown is the relationship of ABR threshold at different frequencies to prestin serum concentration for each rat. Mean +/−95% confidence interval prestin serum concentrations are shows as the dotted and solid lines, respectively.
Figure 16:
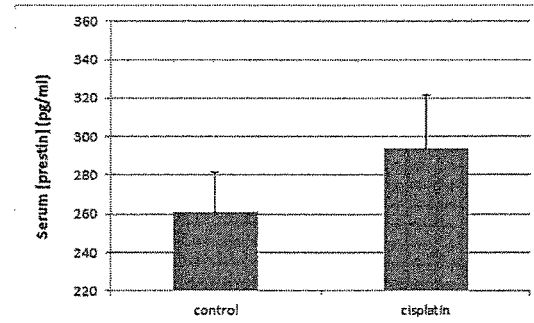
FIG. 16 shows mean serum concentrations of prestin in cisplatin-treated rats compared to controls as in FIG. 15. Cisplatin ototoxicity induces increased serum prestin levels 72 hours after exposure to ototoxic agent.
Figure 17:
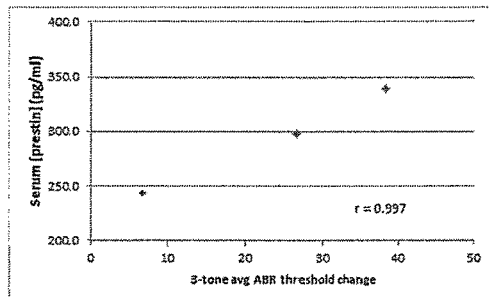
FIG. 17 shows the correlation between the prestin level and hearing loss as measured with ABR (displayed as three-tone average). Serum prestin concentration was strongly correlated with the amount of hearing loss.

In this experiment, three rats were treated with cisplatin (ototoxic agent) and tested (both blood and ABR) 72 hours later. Rats are more vulnerable to ototoxic damage than mice. As shown in FIG. 15, all three rats had significant hearing loss—one was mild and two were moderate to severe. As shown in FIG. 16, the serum prestin level was elevated in the cisplatin-treated rats. As shown in FIG. 17, there was a perfect correlation between the prestin level and hearing loss as measured with ABR. These results demonstrate the value of prestin as an adjunctive diagnostic test in evaluating cochlear damage and hearing loss.

It is an object of diagnostic reagents, methods and kits disclosed herein to provide a number of advantages over currently available diagnostic methods for inner ear disorders such as BPPV: easy blood sample collection; can be done by standard lab or in emergency room setting; does not require a physician to be expert in neurological testing; can provide quick and inexpensive diagnosis of BPPV, for example, and rule out a more serious cause of dizziness like head injury or stroke; can get possible stroke victims the right assessment faster while allowing BPPV patients the ability to avoid expensive and/or unnecessary imaging procedures; improves on current BPPV testing, which is qualitative at best.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of detecting an inner ear disorder in a subject suspected of having the inner ear disorder caused by injurious noise or an ototoxin comprising,
   providing a serum or plasma sample obtained from the subject from an hour to 5 days after exposure to the injurious noise or the ototoxin;
   measuring in an immunoassay a level of prestin (SEQ ID NO: 2) in the serum or plasma sample from the subject;
   determining that the subject is likely to have an inner ear disorder when the level of prestin in the serum or plasma sample is increased by at least 20% compared to a reference prestin level in a reference population that is not suffering from an inner ear disorder; and
   removing the source of the injurious noise or the ototoxin from the subject likely to have an inner ear disorder.

2. The method of claim 1, wherein providing the serum or plasma sample from the subject comprises providing a blood sample from the subject and isolating serum or plasma from the blood sample to obtain the serum or plasma sample.

3. The method of claim 1, wherein the subject is not experiencing detectable injury or damage to the cochlea.

4. The method of claim 1, wherein the subject does not exhibit hearing loss as measured by audiogram.

5. The method of claim 1, wherein the subject is a patient undergoing chemotherapy for cancer treatment, a subject exposed to noise-induced hearing loss in the military, or a subject exposed to the noise or the ototoxin in an occupational setting.

6. The method of claim 1, wherein the hearing disorder is tinnitus, high-frequency hearing loss, or blast-induced hearing loss.

7. The method of claim 1, wherein the reference prestin level is a baseline level from the subject prior to exposure to the noise or the ototoxin, or the reference prestin level is determined from a reference population that is not suffering from an inner ear disorder.

8. The method of claim 7, wherein the baseline level of prestin from the subject is a level determined prior to exposure to the noise, a level determined prior to exposure to the ototoxin, or a level determined in a sample taken from the subject at an earlier point in time.

9. A method of detecting loss of hearing in a subject suspected of exposure to injurious levels of noise or an ototoxin comprising,
   providing a first serum or plasma sample from the subject;
   measuring in an immunoassay a level of prestin (SEQ ID NO:2) in the first serum or plasma sample from the subject;
   exposing the subject to the injurious levels of the noise or the ototoxin;
   providing a second serum or plasma sample from the subject taken from an hour to 5 days after the exposing;
   determining a level of prestin in the second serum or plasma sample from the subject;
   determining that the subject is likely to have an inner ear disorder when the level of prestin is increased by at least 20% in the second serum or plasma sample compared to the first serum or plasma sample; and
   removing the source of the injurious noise or the ototoxin from the subject likely to have an inner ear disorder.

10. The method of claim 9, further comprising measuring an auditory brainstem evoked response (ABR) threshold, a distortion product otoacoustic emission (DPOAE) level, or both in the subject.

11. The method of claim 1, further comprising, when it is determined that the subject is likely to have an inner ear disorder, measuring pure tone audiometry, an auditory brainstem evoked response (ABR) threshold, a distortion product otoacoustic emission (DPOAE) level, or a combination thereof in the subject.

12. The method of claim 9, further comprising, when it is determined that the subject is likely to have an inner ear disorder based on the level of prestin, intervening before development of disabling hearing loss and tinnitus.

13. The method of claim 1, further comprising
measuring a level of otolin-1 (SEQ ID NO: 1) in the serum or plasma sample from the subject, and determining that the subject is likely to have an inner ear disorder when the level of otolin-1 in the serum or plasma sample is greater than 500 pg/mL, or when the level of otolin-1 in the serum or plasma sample is comparable to a level of otolin-1 of a reference population known to have an inner ear disorder.

14. The method of claim 7, further comprising
measuring a level of otolin-1 (SEQ ID NO:1) in the first serum or plasma sample from the subject;
determining a level of otolin-1 in the second serum or plasma sample from the subject; and
determining that the subject is likely to have an inner ear disorder when the level of otolin-1 is increased by at least 20% in the second serum or plasma sample compared to the first serum or plasma sample.

15. A method of treating a subject suspected of having the inner ear disorder caused by injurious noise or an ototoxin comprising,
providing a serum or plasma sample obtained from the subject from an hour to 5 days after exposure to the injurious noise or the ototoxin;
measuring in an immunoassay a level of prestin (SEQ ID NO: 2) in the serum or plasma sample from the subject;
determining that the subject is likely to have an inner ear disorder when the level of prestin in the serum or plasma sample is increased by at least 20% compared to a reference prestin level in a reference population that is not suffering from an inner ear disorder; and
measuring pure tone audiometry, an auditory brainstem evoked response (ABR) threshold, a distortion product otoacoustic emission (DPOAE) level, or a combination thereof in the subject the subject likely to have an inner ear disorder.

* * * * *

SEQUENCE LISTING

```
<160> NUMBER OF SEQ ID NOS: 4

<210> SEQ ID NO 1
<211> LENGTH: 477
<212> TYPE: PRT
<213> ORGANISM: Homo sapiens

<400> SEQUENCE: 1

Met Trp Met Phe Ser Trp Leu Cys Ala Ile Leu Ile Ile Leu Ala Ile
1               5                   10                  15

Ala Gly Met Asn Thr Ile Ala Lys Thr Thr Pro His Thr Lys Phe Thr
            20                  25                  30

Lys Lys Ser Glu Glu Arg Glu Met Pro Lys Gly Leu Lys Pro Ser Ser
        35                  40                  45

Gly Pro Pro Pro Glu Glu Glu Glu Thr Leu Phe Thr Glu Met Ala Glu
    50                  55                  60

Met Ala Glu Pro Ile Thr Lys Pro Ser Ala Leu Asp Ser Val Phe Gly
65                  70                  75                  80

Thr Ala Thr Leu Ser Pro Phe Glu Asn Phe Thr Leu Asp Pro Ala Asp
```

```
                    85                  90                  95
Phe Phe Leu Asn Cys Cys Asp Cys Cys Ser Pro Val Pro Gly Gln Lys
                100                 105                 110
Gly Glu Pro Gly Glu Thr Gly Gln Pro Gly Pro Lys Gly Glu Ala Gly
                115                 120                 125
Asn Leu Gly Ile Pro Gly Pro Pro Gly Val Val Gly Pro Gln Gly Pro
            130                 135                 140
Arg Gly Tyr Lys Gly Glu Lys Gly Leu Lys Gly Glu Arg Gly Asp Gln
145                 150                 155                 160
Gly Val Pro Gly Tyr Pro Gly Lys Pro Gly Ala Gln Gly Glu Pro Gly
                165                 170                 175
Pro Lys Gly Asp Lys Gly Asn Ile Gly Leu Gly Gly Val Lys Gly Gln
                180                 185                 190
Lys Gly Ser Lys Gly Asp Thr Cys Gly Asn Cys Thr Lys Gly Glu Lys
                195                 200                 205
Gly Asp Gln Gly Ala Met Gly Ser Pro Gly Leu His Gly Gly Pro Gly
            210                 215                 220
Ala Lys Gly Glu Lys Gly Glu Met Gly Glu Lys Gly Glu Met Gly Asp
225                 230                 235                 240
Lys Gly Cys Cys Gly Asp Ser Gly Glu Arg Gly Gly Lys Gly Gln Lys
                245                 250                 255
Gly Glu Gly Gly Met Lys Gly Glu Lys Gly Ser Lys Gly Asp Ser Gly
                260                 265                 270
Met Glu Gly Lys Ser Gly Arg Asn Gly Leu Pro Gly Ala Lys Gly Asp
            275                 280                 285
Pro Gly Ile Lys Gly Glu Lys Gly Glu Leu Gly Pro Pro Gly Leu Leu
            290                 295                 300
Gly Pro Thr Gly Pro Lys Gly Asp Ile Gly Asn Lys Gly Val Arg Gly
305                 310                 315                 320
Pro Thr Gly Lys Lys Gly Ser Arg Gly Phe Lys Gly Ser Lys Gly Glu
                325                 330                 335
Leu Ala Arg Val Pro Arg Ser Ala Phe Ser Ala Gly Leu Ser Lys Pro
                340                 345                 350
Phe Pro Pro Pro Asn Ile Pro Ile Lys Phe Glu Lys Ile Leu Tyr Asn
                355                 360                 365
Asp Gln Gly Asn Tyr Ser Pro Val Thr Gly Lys Phe Asn Cys Ser Ile
            370                 375                 380
Pro Gly Thr Tyr Val Phe Ser Tyr His Ile Thr Val Arg Gly Arg Pro
385                 390                 395                 400
Ala Arg Ile Ser Leu Val Ala Gln Asn Lys Lys Gln Phe Lys Ser Arg
                405                 410                 415
Glu Thr Leu Tyr Gly Gln Glu Ile Asp Gln Ala Ser Leu Leu Val Ile
            420                 425                 430
Leu Lys Leu Ser Ala Gly Asp Gln Val Trp Leu Glu Val Ser Lys Asp
            435                 440                 445
Trp Asn Gly Val Tyr Val Ser Ala Glu Asp Asp Ser Ile Phe Thr Gly
            450                 455                 460
Phe Leu Leu Tyr Pro Glu Glu Thr Ser Gly Ile Ser Pro
465                 470                 475

<210> SEQ ID NO 2
<211> LENGTH: 744
<212> TYPE: PRT
<213> ORGANISM: Homo sapiens
```

```
<400> SEQUENCE: 2

Met Asp His Ala Glu Glu Asn Glu Ile Leu Ala Ala Thr Gln Arg Tyr
1               5                   10                  15

Tyr Val Glu Arg Pro Ile Phe Ser His Pro Val Leu Gln Glu Arg Leu
            20                  25                  30

His Thr Lys Asp Lys Val Pro Asp Ser Ile Ala Asp Lys Leu Lys Gln
                35                  40                  45

Ala Phe Thr Cys Thr Pro Lys Lys Ile Arg Asn Ile Ile Tyr Met Phe
        50                  55                  60

Leu Pro Ile Thr Lys Trp Leu Pro Ala Tyr Lys Phe Lys Glu Tyr Val
65                  70                  75                  80

Leu Gly Asp Leu Val Ser Gly Ile Ser Thr Gly Val Leu Gln Leu Pro
                85                  90                  95

Gln Gly Leu Ala Phe Ala Met Leu Ala Ala Val Pro Pro Ile Phe Gly
            100                 105                 110

Leu Tyr Ser Ser Phe Tyr Pro Val Ile Met Tyr Cys Phe Leu Gly Thr
            115                 120                 125

Ser Arg His Ile Ser Ile Gly Pro Phe Ala Val Ile Ser Leu Met Ile
        130                 135                 140

Gly Gly Val Ala Val Arg Leu Val Pro Asp Asp Ile Val Ile Pro Gly
145                 150                 155                 160

Gly Val Asn Ala Thr Asn Gly Thr Glu Ala Arg Asp Ala Leu Arg Val
                165                 170                 175

Lys Val Ala Met Ser Val Thr Leu Leu Ser Gly Ile Ile Gln Phe Cys
            180                 185                 190

Leu Gly Val Cys Arg Phe Gly Phe Val Ala Ile Tyr Leu Thr Glu Pro
            195                 200                 205

Leu Val Arg Gly Phe Thr Thr Ala Ala Ala Val His Val Phe Thr Ser
        210                 215                 220

Met Leu Lys Tyr Leu Phe Gly Val Lys Thr Lys Arg Tyr Ser Gly Ile
225                 230                 235                 240

Phe Ser Val Val Tyr Ser Thr Val Ala Val Leu Gln Asn Val Lys Asn
                245                 250                 255

Leu Asn Val Cys Ser Leu Gly Val Gly Leu Met Val Phe Gly Leu Leu
            260                 265                 270

Leu Gly Gly Lys Glu Phe Asn Glu Arg Phe Lys Glu Lys Leu Pro Ala
            275                 280                 285

Pro Ile Pro Leu Glu Phe Phe Ala Val Val Met Gly Thr Gly Ile Ser
        290                 295                 300

Ala Gly Phe Asn Leu Lys Glu Ser Tyr Asn Val Asp Val Val Gly Thr
305                 310                 315                 320

Leu Pro Leu Gly Leu Leu Pro Pro Ala Asn Pro Asp Thr Ser Leu Phe
                325                 330                 335

His Leu Val Tyr Val Asp Ala Ile Ala Ile Ala Ile Val Gly Phe Ser
            340                 345                 350

Val Thr Ile Ser Met Ala Lys Thr Leu Ala Asn Lys His Gly Tyr Gln
            355                 360                 365

Val Asp Gly Asn Gln Glu Leu Ile Ala Leu Gly Leu Cys Asn Ser Ile
        370                 375                 380

Gly Ser Leu Phe Gln Thr Phe Ser Ile Ser Cys Ser Leu Ser Arg Ser
385                 390                 395                 400

Leu Val Gln Glu Gly Thr Gly Gly Lys Thr Gln Leu Ala Gly Cys Leu
```

```
                405                 410                 415
Ala Ser Leu Met Ile Leu Leu Val Ile Leu Ala Thr Gly Phe Leu Phe
            420                 425                 430

Glu Ser Leu Pro Gln Ala Val Leu Ser Ala Ile Val Ile Val Asn Leu
        435                 440                 445

Lys Gly Met Phe Met Gln Phe Ser Asp Leu Pro Phe Phe Trp Arg Thr
    450                 455                 460

Ser Lys Ile Glu Leu Thr Ile Trp Leu Thr Thr Phe Val Ser Ser Leu
465                 470                 475                 480

Phe Leu Gly Leu Asp Tyr Gly Leu Ile Thr Ala Val Ile Ile Ala Leu
                485                 490                 495

Leu Thr Val Ile Tyr Arg Thr Gln Ser Pro Ser Tyr Lys Val Leu Gly
            500                 505                 510

Lys Leu Pro Glu Thr Asp Val Tyr Ile Asp Ile Asp Ala Tyr Glu Glu
        515                 520                 525

Val Lys Glu Ile Pro Gly Ile Lys Ile Phe Gln Ile Asn Ala Pro Ile
    530                 535                 540

Tyr Tyr Ala Asn Ser Asp Leu Tyr Ser Asn Ala Leu Lys Arg Lys Thr
545                 550                 555                 560

Gly Val Asn Pro Ala Val Ile Met Gly Ala Arg Arg Lys Ala Met Arg
                565                 570                 575

Lys Tyr Ala Lys Glu Val Gly Asn Ala Asn Met Ala Asn Ala Thr Val
            580                 585                 590

Val Lys Ala Asp Ala Glu Val Asp Gly Glu Asp Ala Thr Lys Pro Glu
        595                 600                 605

Glu Glu Asp Gly Glu Val Lys Tyr Pro Pro Ile Val Ile Lys Ser Thr
    610                 615                 620

Phe Pro Glu Glu Met Gln Arg Phe Met Pro Pro Gly Asp Asn Val His
625                 630                 635                 640

Thr Val Ile Leu Asp Phe Thr Gln Val Asn Phe Ile Asp Ser Val Gly
                645                 650                 655

Val Lys Thr Leu Ala Gly Ile Val Lys Glu Tyr Gly Asp Val Gly Ile
            660                 665                 670

Tyr Val Tyr Leu Ala Gly Cys Ser Ala Gln Val Val Asn Asp Leu Thr
        675                 680                 685

Arg Asn Arg Phe Phe Glu Asn Pro Ala Leu Trp Glu Leu Leu Phe His
    690                 695                 700

Ser Ile His Asp Ala Val Leu Gly Ser Gln Leu Arg Glu Ala Leu Ala
705                 710                 715                 720

Glu Gln Glu Ala Ser Ala Pro Pro Ser Gln Glu Asp Leu Glu Pro Asn
                725                 730                 735

Ala Thr Pro Ala Thr Pro Glu Ala
            740

<210> SEQ ID NO 3
<211> LENGTH: 493
<212> TYPE: PRT
<213> ORGANISM: Homo sapiens

<400> SEQUENCE: 3

Met Ile Ala Phe Leu Leu Thr Ser Val Leu Met Ile Pro His Ala Gly
1               5                   10                  15

Gly His Pro Leu Asp Thr Pro His Leu Pro Gln Glu Leu Pro Pro Gly
            20                  25                  30
```

-continued

```
Leu Pro Asn Asn Ile Asn Ile Thr Phe Phe Ser Gly Met Phe Lys Asn
             35                  40                  45

Val Glu Ser Val Ala Glu Ile Phe Asp Cys Leu Gly Pro His Phe Thr
 50                  55                  60

Trp Leu Gln Ala Val Phe Thr Asn Phe Pro Val Leu Ile Gln Phe Val
 65                  70                  75                  80

Asn Gly Met Lys Cys Val Ala Gly Leu Cys Pro Arg Asp Phe Glu Asp
                 85                  90                  95

Tyr Gly Cys Thr Cys Arg Phe Glu Met Glu Gly Leu Pro Val Asp Glu
                100                 105                 110

Ser Asp Ser Cys Cys Phe Gln His Arg Arg Cys Tyr Glu Glu Ala Ala
             115                 120                 125

Glu Met Asp Cys Leu Gln Asp Pro Ala Lys Leu Ser Thr Glu Val Asn
 130                 135                 140

Cys Val Ser Lys Lys Ile Ile Cys Glu Ser Lys Asp Asn Cys Glu His
145                 150                 155                 160

Leu Leu Cys Thr Cys Asp Lys Ala Ala Ile Glu Cys Leu Ala Arg Ser
                165                 170                 175

Ser Leu Asn Ser Ser Leu Asn Leu Leu Asp Thr Ser Phe Cys Leu Ala
            180                 185                 190

Gln Thr Pro Glu Thr Thr Ile Lys Glu Asp Leu Thr Thr Leu Leu Pro
        195                 200                 205

Arg Val Val Pro Val Glu Pro Thr Asp Thr Ser Leu Thr Ala Leu Ser
    210                 215                 220

Gly Glu Val Ala Ala Glu Thr Glu Ala Asp Arg Leu Ile Thr Leu Ser
225                 230                 235                 240

Lys Lys Lys Ala Gly His Asp Gln Glu Gly Val Gly Ala Ala Arg Ala
                245                 250                 255

Thr Ser Pro Pro Gly Ser Ala Glu Ile Val Ala Thr Arg Val Thr Ala
            260                 265                 270

Lys Ile Val Thr Leu Val Pro Ala Gly Ile Lys Ser Leu Gly Leu Ala
        275                 280                 285

Val Ser Ser Val Glu Asn Asp Pro Glu Glu Thr Thr Glu Lys Ala Cys
    290                 295                 300

Asp Arg Phe Thr Phe Leu His Leu Gly Ser Gly Asp Asn Met Gln Val
305                 310                 315                 320

Met Pro Gln Leu Gly Glu Met Leu Phe Cys Leu Thr Ser Arg Cys Pro
                325                 330                 335

Glu Glu Phe Glu Ser Tyr Gly Cys Tyr Cys Gly Gln Glu Gly Arg Gly
            340                 345                 350

Glu Pro Arg Asp Asp Leu Asp Arg Cys Cys Leu Ser His His Cys Cys
        355                 360                 365

Leu Glu Gln Val Arg Arg Leu Gly Cys Leu Leu Glu Arg Leu Pro Trp
    370                 375                 380

Ser Pro Val Val Cys Val Asp His Thr Pro Lys Cys Gly Gly Gln Ser
385                 390                 395                 400

Leu Cys Glu Lys Leu Leu Cys Ala Cys Asp Gln Thr Ala Ala Glu Cys
                405                 410                 415

Met Thr Ser Ala Ser Phe Asn Gln Ser Leu Lys Ser Pro Ser Arg Leu
            420                 425                 430

Gly Cys Pro Gly Gln Pro Ala Ala Cys Glu Asp Ser Leu His Pro Val
        435                 440                 445

Pro Ala Ala Pro Thr Leu Gly Ser Ser Ser Glu Glu Asp Ser Glu Glu
```

-continued

```
                450                 455                 460
Asp Pro Pro Gln Glu Asp Leu Gly Arg Ala Lys Arg Phe Leu Arg Lys
465                 470                 475                 480

Ser Leu Gly Pro Leu Gly Ile Gly Pro Leu His Gly Arg
                485                 490

<210> SEQ ID NO 4
<211> LENGTH: 109
<212> TYPE: PRT
<213> ORGANISM: Homo sapiens

<400> SEQUENCE: 4

Met Ser Ile Thr Asp Val Leu Ser Ala Asp Ile Ala Ala Ala Leu
1               5                   10                  15

Gln Glu Cys Arg Asp Pro Asp Thr Phe Glu Pro Gln Lys Phe Phe Gln
                20                  25                  30

Thr Ser Gly Leu Ser Lys Met Ser Ala Asn Gln Val Lys Asp Val Phe
            35                  40                  45

Arg Phe Ile Asp Asn Asp Gln Ser Gly Tyr Leu Asp Glu Glu Leu
    50                  55                  60

Lys Phe Leu Gln Lys Phe Glu Ser Gly Ala Arg Glu Leu Thr Glu
65                  70                  75                  80

Ser Glu Thr Lys Ser Leu Met Ala Ala Asp Asn Asp Gly Asp Gly
                85                  90                  95

Lys Ile Gly Ala Glu Glu Phe Gln Glu Met Val His Ser
                100                 105
```